(12) United States Patent
Kohayakawa

(10) Patent No.: US 6,685,318 B2
(45) Date of Patent: Feb. 3, 2004

(54) OPHTHALMOLOGIC APPARATUS

(75) Inventor: Yoshimi Kohayakawa, Tochigi-Ken (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/224,587

(22) Filed: Aug. 21, 2002

(65) Prior Publication Data

US 2003/0025875 A1 Feb. 6, 2003

Related U.S. Application Data

(63) Continuation of application No. 09/783,550, filed on Feb. 15, 2001, now abandoned.

(30) Foreign Application Priority Data

Feb. 24, 2000 (JP) .......................................... 2000-048126

(51) Int. Cl.⁷ ................................................ A61B 3/14
(52) U.S. Cl. ...................................................... 351/208
(58) Field of Search ................................ 351/204, 205, 351/206, 208, 209, 210, 221, 211, 246, 243; 348/78; 396/51

(56) References Cited

U.S. PATENT DOCUMENTS

| | | | |
|---|---|---|---|
| 4,609,287 A | 9/1986 | Kohayakawa | 356/124 |
| 4,697,895 A | 10/1987 | Sekiguchi et al. | 351/243 |
| 4,704,012 A | 11/1987 | Kohayakawa et al. | 350/516 |
| 4,820,037 A | 4/1989 | Kohayakawa et al. | 351/211 |
| 4,825,873 A | 5/1989 | Kohayakawa | 128/648 |
| 4,826,315 A | 5/1989 | Kohayakawa | 356/125 |
| 4,830,483 A | 5/1989 | Kohayakawa | 351/221 |
| 5,031,623 A | 7/1991 | Kohayakawa et al. | 128/648 |
| 5,037,194 A | 8/1991 | Kohayakawa et al. | 351/224 |
| 5,144,346 A | 9/1992 | Nakamura et al. | 351/208 |
| 5,231,430 A | 7/1993 | Kohayakawa | 351/243 |
| 5,231,460 A | 7/1993 | Kohayakawa | 356/125 |
| 5,237,351 A | 8/1993 | Kohayakawa et al. | 351/243 |
| 5,249,003 A | 9/1993 | Kohayakawa | 351/211 |
| 5,280,313 A | 1/1994 | Kohayakawa | 351/211 |
| 5,325,134 A | 6/1994 | Kohayakawa | 351/212 |
| 5,420,650 A | 5/1995 | Kohayakawa | 351/206 |
| 5,483,305 A | 1/1996 | Kohayakawa | 351/243 |
| 5,506,632 A | 4/1996 | Kohayakawa | 351/205 |
| 5,523,808 A | 6/1996 | Kohayakawa | 351/210 |
| 5,523,809 A | 6/1996 | Kohayakawa | 351/211 |
| 5,585,872 A | 12/1996 | Kohayakawa | 351/212 |
| 5,657,116 A | 8/1997 | Kohayakawa | 356/124 |
| 5,675,399 A | 10/1997 | Kohayakawa | 351/237 |
| 5,696,573 A | 12/1997 | Miwa | 351/208 |

(List continued on next page.)

FOREIGN PATENT DOCUMENTS

JP  9-094227  4/1997

*Primary Examiner*—George Manuel
(74) *Attorney, Agent, or Firm*—Fitzpatrick, Cella, Harper & Scinto

(57) ABSTRACT

For improving the operability of the apparatus, the ophthalmologic apparatus of the invention includes a measuring optical system which optically measures an eye to be examined, a detection system which detects alignment information of the eye for the measurement, a driving mechanism which moves the measuring optical system relative to the eye, an operating device which allows an operator to manually control the driving mechanism in order to move the measuring optical system, and a controller that controls the driving mechanism to perform alignment of the measuring optical system with respect to the eye, in a plurality of modes including a first mode executing automatic alignment within a predetermined range based on the alignment information of the detection system and a second mode executing manual alignment within a range broader than the predetermined range based on the operation of the operation device, wherein the controller automatically changes its operation between the first mode and the second mode based on a predetermined event.

17 Claims, 7 Drawing Sheets

U.S. PATENT DOCUMENTS

| | | | |
|---|---|---|---|
| 5,713,047 A | 1/1998 | Kohayakawa | 396/18 |
| 5,777,718 A | 7/1998 | Kohayakawa | 351/211 |
| 5,781,275 A | 7/1998 | Kohayakawa | 351/211 |
| 5,825,460 A | 10/1998 | Kohayakawa | 351/237 |
| 5,847,805 A | 12/1998 | Kohayakawa et al. | 351/210 |
| 5,903,336 A | 5/1999 | Kohayakawa | 351/245 |
| 6,033,074 A | 3/2000 | Miyake et al. | 351/212 |
| 6,132,046 A * | 10/2000 | Iijima | 351/208 |
| 6,304,723 B1 | 10/2001 | Kohayakawa | 396/18 |
| 6,439,719 B2 * | 8/2002 | Hayashi et al. | 351/208 |

* cited by examiner

OPHTHALMOLOGIC APPARATUS

This application is a continuation of U.S. patent application Ser. No. 09/783,550 filed on Feb. 15, 2001 now abandoned.

BACKGROUND OF THE INVENTION

1. Field of the Invention

This invention relates to an ophthalmologic apparatus such as an autorefractometer used for the measurement of an eye to be examined in a hospital or an optician's store.

2. Related Background Art

There are known an ophthalmologic apparatus for effecting auto-alignment after manual alignment, and an ophthalmologic apparatus which can select manual alignment and auto-alignment. However, in the ophthalmologic apparatus for effecting auto-alignment after manual alignment, when alignment becomes impossible due to some cause or other after auto-alignment has been started, alignment must be manually effected again from the first. Also, after auto-alignment has been started, if alignment is manually effected without noticing it, measurement will sometimes become impossible. Also, in an ophthalmologic apparatus capable of effecting both manual alignment and auto-alignment, the changeover between the manual operation and the automatic operation is cumbersome, and an improvement in operability is required.

SUMMARY OF THE INVENTION

The present invention aims at improvements in the ophthalmologic apparatuses according to the prior art and a primary object thereof is to provide an ophthalmologic apparatus excellent in operability. Another object of the present invention is to provide an ophthalmologic apparatus in which a smooth shift is possible between manual alignment and auto-alignment. Still another object of the present invention is to provide an ophthalmologic apparatus that quickly and reliably makes alignment and measurement possible. Yet still another object of the present invention is to provide an ophthalmologic apparatus provided with an optical element with a prism that makes alignment possible by a simple construction.

The ophthalmologic apparatus according to the present invention for achieving the above objects is an ophthalmologic apparatus comprising a measuring optical system that optically measures an eye to be examined, a detection system that detects alignment information of the eye for the measurement, a driving mechanism that moves the measuring optical system relative to the eye, an operating device that allows an operator to manually control the driving mechanism in order to move the measuring optical system, and a controller that controls the driving mechanism to perform alignment of the measuring optical system with respect to the eye, with a plurality of modes including a first mode executing alignment within a predetermined range based on the alignment information of the detection system and a second mode executing manual alignment within a range broader than the predetermined range based on the operation of the operation device, wherein the controller automatically changes between the first mode and the second mode based on a predetermined event.

Further objects and forms of the present invention will become apparent from the following description of some embodiments of the invention.

DESCRIPTION OF THE PREFERRED EMBODIMENTS

Figure 1:
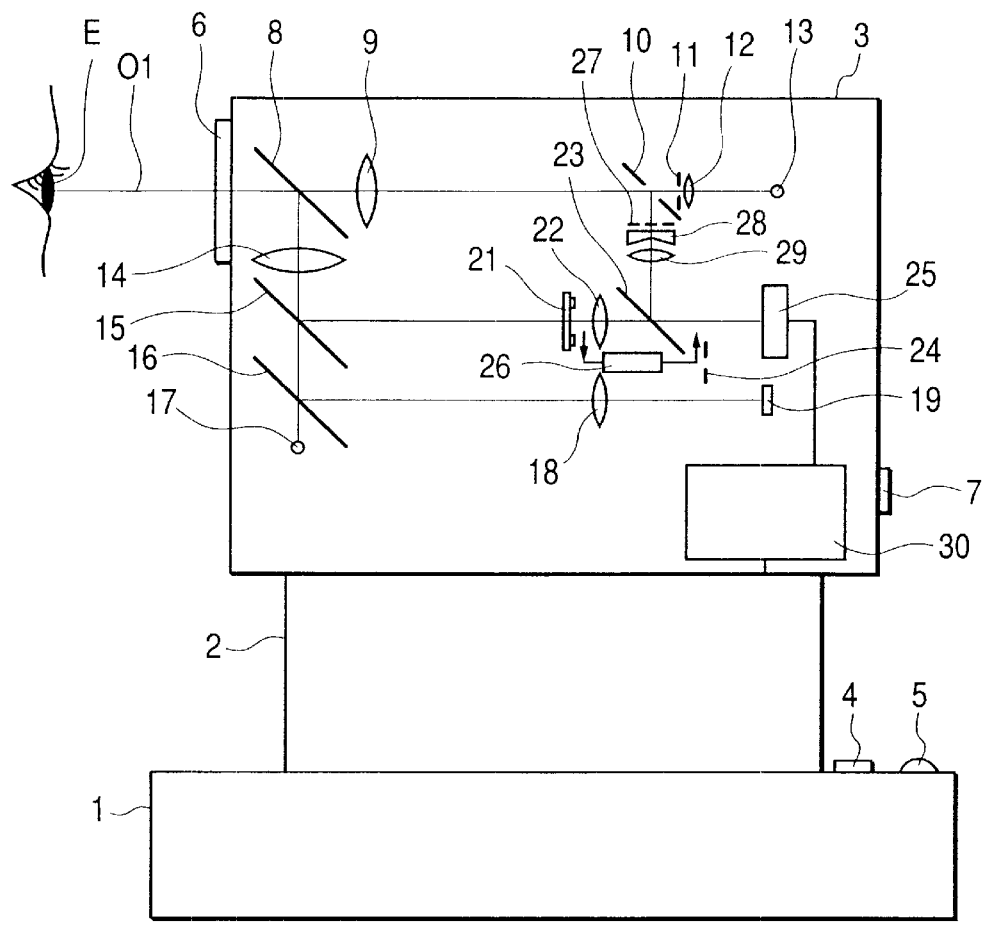
FIG. 1 shows the construction of an ophthalmologic apparatus to which the present invention is applied.

FIG. 1 shows an ophthalmologic apparatus to which the present invention is applied, herein a compound machine of a refractometer for measuring the eye refractive power of an eye to be examined and an auto-keratometer for effecting the measurement of the cornea of the eye to be examined. The present invention is not restricted thereto, but is also applicable to various ophthalmologic apparatuses (such as a tonometer and a fundus examining apparatus) in which the alignment of an optical system relative to an eye to be examined is necessary.

On a base 1, there is provided a driving mechanism 2 including three motors, and a measuring unit 3 containing a measuring optical system therein is mounted on the driving mechanism 2. The driving mechanism 2 drives the measuring unit 3 in any three-dimensional direction. On the operator side (the right side as viewed in FIG. 1) of the base 1, there are provided a measuring switch 4 and an operating device 5 such as a track ball or a joy stick. A ring light source 6 for cornea measurement is provided on the panel of the eye to be examined E side (the left side as viewed in FIG. 1) of the measuring unit 3, and a mode changeover device 7 is provided on the panel of the operator side thereof.

Figure 2:
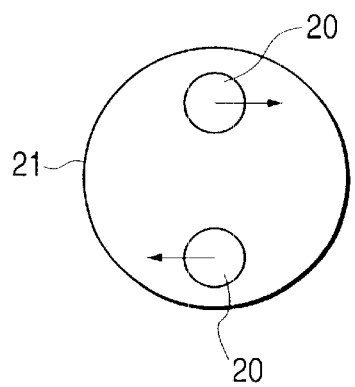
FIG. 2 is a front view of an optical element with a prism used for alignment detection.

On an optical path 01 behind the ring light source 6, there are successively arranged a dichroic mirror 8 reflecting visible light, a lens 9, an apertured mirror 10, a stop 11 conjugate with the pupil, a lens 12 and a light source 13 for refraction measurement. On the optical path in the incidence direction of the dichroic mirror 8, there are arranged an objective lens 14, a half mirror 15, a dichroic mirror 16 reflecting visible light, and a light source 17 for alignment, and the light source 17 for alignment is disposed near the focus of the objective lens 14. On the optical path in the reflecting direction of the dichroic mirror 16, there are disposed a diopter varying lens 18 and a fixation target 19. On the optical path in the reflecting direction of the half mirror 15, there are successively arranged an optical element 21 for alignment measurement selectively insertable into the optical path, a lens 22, a dichroic mirror 23, a stop 24 for cornea measurement selectively insertable into the optical path, and an area sensor (an array sensor such as a CCD) 25. FIG. 2 shows the details of the optical element 21. It is of such structure that two wedge prisms 20 are attached to the surface of a light-transmitting substrate, and has the function of deflecting and separating part of light incident on the optical element 21 by the wedge prisms 20. An actuator 26 including a plurality of solenoids is provided to retractably insert the optical element 21 and the stop 24 into the optical path. On the optical path in the reflecting direction of the apertured mirror 10, there are arranged a six-hole stop 27 conjugate with the pupil, a separating prism 28 and a lens 29, and this optical path leads to the dichroic mirror 23. The output of the area sensor 25 is electrically connected to a controller 30 including a microprocessor, and the output of the controller 30 in turn is connected to the driving mechanism 2. The measuring switch 4, the operating device 5 and the mode changeover device 7 are also electrically connected to the controller 30.

In the above-described construction, the measuring unit 3 is three-dimensionally moved on the base 1 by the driving mechanism 2, whereby the alignment of the measuring optical system relative to the eye to be examined E is effected. A beam from the light source 13 for refraction measurement passes through the lens 12, the stop 11, the apertured mirror 10, the lens 9 and the dichroic mirror 8, and is projected onto the fundus of the eye to be examined E. The reflected light from the fundus of the eye returns along the same optical path is reflected by the apertured mirror 10, passes through the six-hole stop 27, the separating prism 28 and the lens 29, is reflected by the dichroic mirror 23 and is received by the area sensor 25. The six positions of the received beam are calculated by the controller 30 to thereby calculate the eye refraction value. During the measurement of the eye to be examined, the fixation target 19 is presented on the eye to be examined E through the diopter varying lens 18, the dichroic mirror 16, the half mirror 15, the objective lens 14 and the dichroic mirror 8. Also, the front eye part of the eye to be examined E is imaged on the area sensor 25 by an imaging optical system including the objective lens 14 and the lens 22. This imaging optical system is used for cornea measurement as well as for the alignment of the front eye part.

The optical element 21 and the stop 24 are exclusively put into and out of the optical path by the actuator 26. That is, during alignment, the optical element 21 is inserted into the optical path and the stop 24 is put out of the optical path. On the other hand, during cornea measurement, the optical element 21 is put out of the optical path and in operative association therewith, the stop 24 is inserted into the optical path. Actuators 26 may be provided discretely for the optical element 21 and the stop and be individually driven.

The optical element 21 deflects transmitted light in the left and right directions as indicated by arrows in FIG. 2 by the two wedge prisms 20 provided thereon. The upper wedge prism 20 has such a cross-sectional shape that it deflects the beam to the right side as viewed in FIG. 2, and the lower wedge prism 20 has such a cross-sectional shape that it deflects the beam to the left side as viewed in FIG. 2. The other portion than the wedge prisms 20 does not deflect the light beam but transmits the beam and makes the beam travel rectilinearly. As a result, the beam incident on the wedge prisms 20 and the other beam are separated (divided). The number of the wedge prisms need not be two, but if the algorithm of signal processing, which will be described later, is changed, the number of the wedge prisms may be three, four, . . . or one and the detection of alignment state will be possible.

Figure 3:
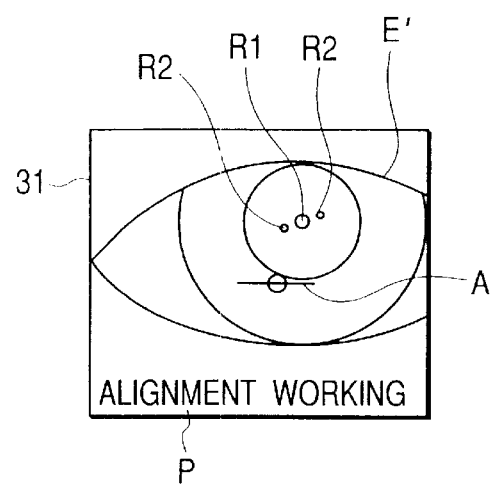
FIG. 3 shows an example of the display by a display.

FIG. 3 shows an example of the display by a display 31, and the output image of the area sensor 25 is displayed. Corneal reflected images R1 and R2 by the light source 17 for alignment are displayed on a front eye part image E', and further an alignment mark A is displayed. A small circle at the center of the alignment mark A coincides with the optical axis. Here, the corneal reflected images R2 are provided by a beam deflected by the wedge prisms 20 on the optical element 21, and the corneal reflected image R1 is provided by a beam not deflected but rectilinearly travelling through the optical element 21. Unless the corneal reflected image R1 and the area sensor 25 are conjugate with each other, the two corneal reflected images R2 rotate about R1 as shown, but if they become conjugate with each other, the line linking the two corneal reflected images R2 together will become a horizontal line. Consequently, if three-dimensional alignment is perfect, all the corneal reflected images R1 and R2 lie in a straight line on the horizontal alignment mark A, and R1 overlaps the center of the alignment mark A.

The controller 30 calculates the positions of the corneal reflected images R2 and R1 on the basis of a signal from the area sensor 25 to thereby calculate the alignment state, i.e., the degree (amount) and direction of the positional deviation, of the eye to be examined E relative to the optical system. The wedge prisms 20 are sufficiently small as compared with the size of an opening around them and therefore, it does not happen that a front eye part image weak in reflection is reflected in overlapping relationship therewith. Also, these beams passing through the optical element 21 are deep in depth of focus and therefore, even if the distance therebetween is considerably great, it is possible to reflect the corneal reflected image R2, and the alignment state can be reliably recognized by calculation. The controller 30 drives the driving mechanism 2 on the basis of the detected alignment state in such a direction and amount of movement that the deviation becomes null, and executes auto-alignment. The mode in which the controller 30 automatically controls the driving mechanism 2 on the basis of the detection of the alignment state so as to eliminate this alignment deviation is called the "auto mode". In contrast, the mode in which automatic control is not effected, but the driving mechanism 2 is driven on the basis of a signal from the operating device 5 is called the "manual mode".

A description will not be provided of sequence that the apparatus according to the present embodiment has, i.e., a sequence in which a shift is automatically made between the manual mode and the auto mode and alignment is effected, and a sequence in which a measurement is automatically started which alignment is completed.

At the start of the alignment relative to the eye to be examined, a usually great positional deviation takes place beyond a predetermined range within which auto-alignment is possible, and the display as shown in FIG. 3 cannot be obtained. Consequently at first, the auto mode does not operate and an operator manually effects alignment roughly by the manual mode. That is, the operator operates the operating device 5 to thereby move the measuring unit 3 while looking at the eye to be examined E on the display 31, and adjusts the measuring unit so that the pupil may come into the screen as shown in FIG. 3. The controller 30 controls the driving mechanism 2 on the basis of the operation of the operating device 5 and in the meantime, the controller 30 continues the detection of the alignment state from the signal of the area sensor 25. When the detected amount of alignment deviation has come to lie in the predetermined range within which auto-alignment is possible, the controller 30 automatically shifts the apparatus from the manual mode to the auto mode to thereby start the auto-alignment operation.

When the auto-alignment operation has ben entered, characters "ALIGNMENT WORKING" are indicated on the display 31 as shown in FIG. 3, thereby informing the operator that auto-alignment is being executed. When the operation confirms this indication and releases the operating device 5, alignment will be automatically completed with nothing being operated thereafter. The way of indication on the display 31 is not limited to this, but may be by a change in the flash, luminance, color or the like of the display. Also, while in the present embodiment, the character indication on the display 31 is an indicator for enabling the operator to distinguish between the auto/manual modes, visual or aural indication techniques may be used. For example, an indicator comprising a lamp for exclusive use may be provided at a location on the apparatus which can be seen by the operator so as to indicate the distinction between the auto/manual modes to the operator by the turning-on thereof or a change in the color thereof. Otherwise, some kind of sound may be used as the indicator. At any rate, it is important to indicate by the indicator that a shift has been made from the manual mode to the auto mode, thereby informing the operator that the operation thereafter is not necessary.

The controller 30, if the sequentially calculated alignment deviation is within a range smaller than a prescribed value, judges that the alignment has been completed. Subsequently, it automatically starts the measurement of the eye to be examined (the measurement of eye refractive power and cornea shape). That is, even if the operator does not depress the measuring switch 4, the measurement of the eye to be examined is automatically started after the completion of the auto-alignment and therefore, operability is good. During the measurement, the optical element 21 is retracted out of the optical path by the actuator 26, the stop 24 is inserted, the ring light source 6 is turned on and the corneal reflected image therefrom is received by the area sensor 21, and the signal thereof is calculated by the controller 30 to thereby find the measured value of the eye to be examined.

On the other hand, even if auto-alignment is working, when the operator operates the operating device 5, priority is given to the manual operation. That is, when the operator desires the manual operation for some reason or other, the auto mode becomes off and the manual mode is automatically restarted. At this time, the indicator changes and therefore, the operator can confirm that the auto mode has been released. Even if the manual mode is working, when the operator discontinues the operator of the device 5 and the signal from the operating device 5 is interrupted for a predetermined time (e.g. one second), the auto mode is automatically restarted and auto-alignment driving is resumed again. Also during the manual mode, the controller 30 continues to recognize the alignment state from the signal of the area sensor 25, and when it judges that the alignment has been completed, it immediately starts measurement. When the operator depresses the measuring switch 4 even if the alignment is not yet completed, measurement is effected with priority given thereto. As described above, the auto mode and the manual mode are automatically changed over without the changeover operation being performed and therefore, an ophthalmologic apparatus excellent in operability is provided. Also, priority is given to the operators' intention (operation) and therefore safety is high. This sequence is effective when for example, the eye to be examined has an exceptional characteristic and the corneal reflected images R2 are not sufficiently obtained and auto-alignment does not work well.

While the sequence in which the manual/auto modes are automatically changed over has been described above, a manual fixed mode can be provided if the operator designates it by the mode changeover device 7. When the manual fixed mode is selected, the auto mode does not work and the controller 30 moves the position of the measuring unit 3 by the driving mechanism 2 on the basis of the signal of the operating device 5. The operator visually observes the display 31 and effects alignment, and when he confirms perfect alignment, the apparatus carries out the measurement of the eye to be examined if the operator depresses the measuring switch 4. That is, the auto mode does not work at all from the first to the last.

Figure 4:
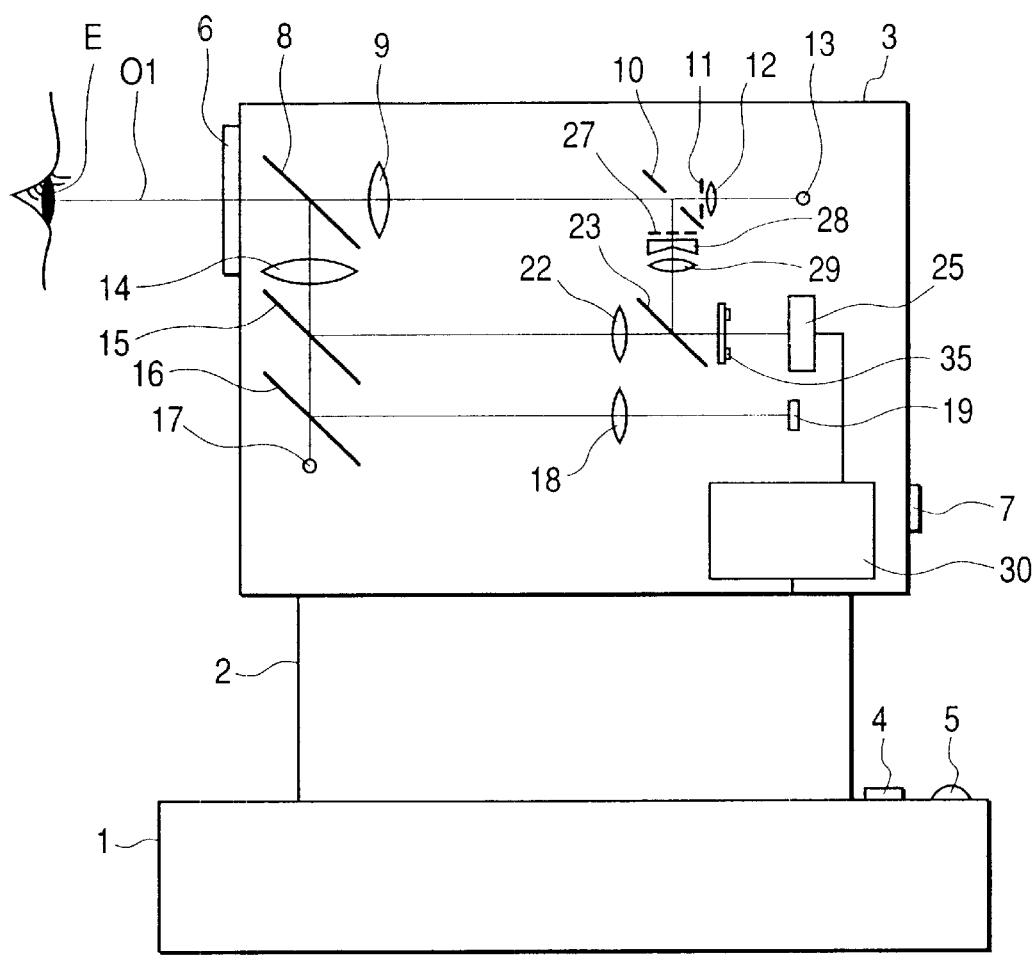
FIG. 4 shows the construction of another embodiment of the ophthalmologic apparatus.

A modification of the above-described embodiment will now be described. FIG. 4 shows the general construction of the modification, and in FIG. 4, the same reference numerals as those in FIG. 1 designate the same members. As compared with the embodiment of FIG. 1, this modification differs in the structure, and location of an optical element 35, and greatly differs in that the actuator for moving it is unnecessary. The ring light source 6 for cornea measurement illuminates the cornea of the eye to be examined E by parallel light, and the optical element 35 is disposed near the focus point of the imaging optical system of the lens 14 and the lens 22.

Figure 5:
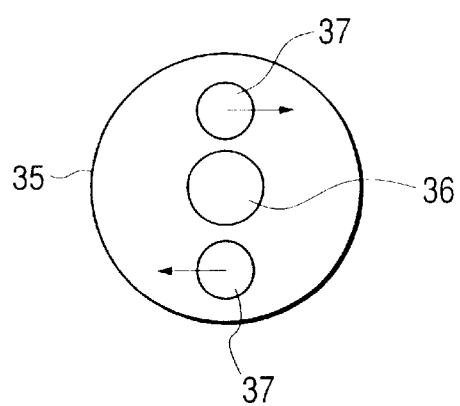
FIG. 5 is a front view of an optical element in FIG. 4.

FIG. 5 shows a front view of the optical element 35. An opening 36 for transmitting therethrough the wavelength of the ring light source 6 for measurement is provided in the central portion of a transmissive substrate, and dichroic film having the characteristic of not transmitting the wavelength of the ring light source 6 therethrough but transmitting therethrough the wavelength of the light source 17 for alignment is formed around the opening 36. The opening 36 functions as a stop during cornea measurement and therefore, the stop 24 in the aforedescribed embodiment is unnecessary. Openings comprising two wedge prisms 37 used for alignment are formed outside the opening 36. These wedge prisms 37 are located around an opening in an imaging optical system comprising the objective lens 14 and the lens 22. The number of the wedge prisms is not limited to two as previously described.

According to the construction of the present embodiment, the wavelength of the light source 17 for alignment is transmitted through all portions of the optical element 35 and therefore, during both of measurement and alignment, the optical element 35 may be placed in the optical path and need not be moved. An actuator therefor becomes unnecessary and the construction is simple and high in reliability.

Further, as the imaging optical system of the lens 14 and the lens 22, and the area sensor 25 are used both for three-dimensional alignment and cornea measurement of the construction is simple.

A third embodiment will now be described with reference to FIGS. 10 to 12.

Figure 10:
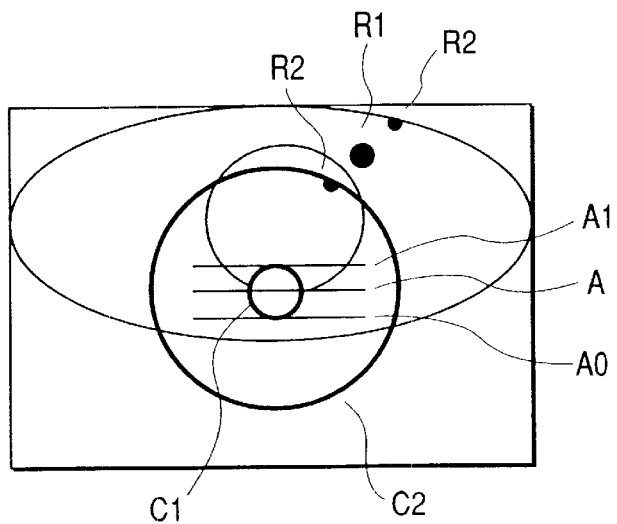
FIG. 10 shows a monitor screen representing the state before in the third embodiment, changeover is done from a manual mode to an auto mode.
Figure 11:
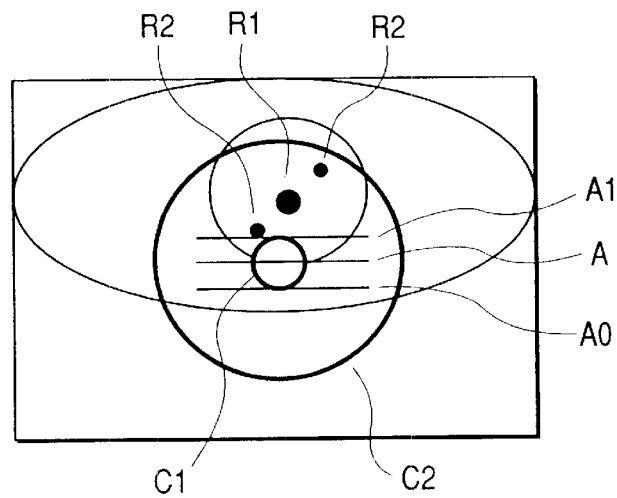
FIG. 11 shows a monitor screen representing the state when in the third embodiment, changeover is done from the manual mode to the auto mode.

FIGS. 10 and 11 show monitor screens representing states before and after the mode is changed over to the auto mode, and at the time of completing the auto alignment, when alignment has been started in the manual mode.

R1 and R2 designate corneal reflected images described in connection with FIG. 3. A denotes an alignment mark electrically synthesized at a predetermine position on the monitor by the aforementioned calculating means 33 described also in connection with FIG. 3. A0 and A1 designate marks indicative of the allowable ranges of alignment, and like A, they are electrically synthesized. When R1 and R2 are displayed between A0 and A1, it indicates that the distance between the eye to be examined and the measuring optical system has been adjusted to within an allowable range. Of course, the above-described determination is effected by detecting the coordinate positions of R1 and R2 from the output image of the area sensor 25 by the calculating means 30, and comparing the positional relations thereof with A1 and A2.

C1 denotes a mark existing at the center of the alignment mark and representative of the allowable area of alignment adjustment. Like A, A0 and A1, it is an electrically synthesized signal.

When R1 has entered the area C1, it is judged by the calculating means 30 that the horizontal and vertical adjustment of alignment has been completed.

C2 designates a mark representative of an auto alignment area, and like C1, it is an electrically synthesized-signal, and the following processing is effected by the calculating means 30.

When the reflected image R1 has entered the area C2, it is judged that there is obtained a reflected image signal of high reliability capable of being subjected auto alignment, and the mode is changed over from the manual mode to the auto mode. When the mode is changed over to the auto mode, the calculating means 30 determines the position of R1 and the position of C1, and determines the positional relation between R1 and R2 and between A0 and A1 in a direction perpendicular to the screen, and the driving mechanism 2 is moved until R1 enters the interior of C1 an R1 and R2 come into between A0 and A1.

Figure 12:
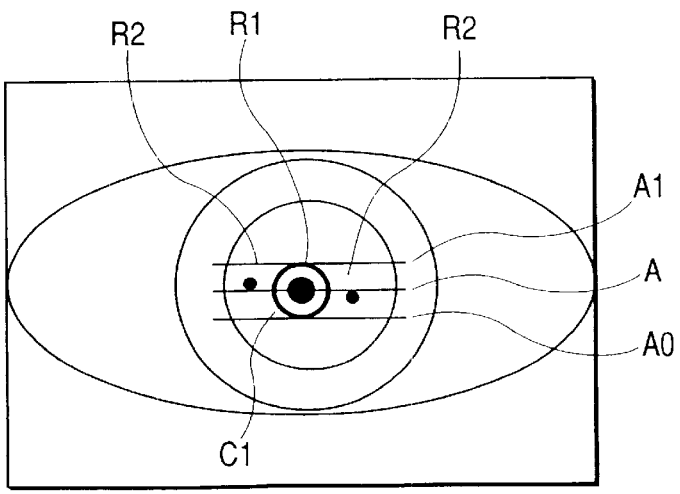
FIG. 12 shows a monitor screen representing the state in which in the third embodiment, alignment has been completed and measurement has become possible.

When as shown in FIG. 12, the reflected image R1 enters the interior of C1, and R1 and R2 come into between A0 and A1, alignment is completed and the driving mechanism 2 is stopped and auto measurement is started.

Of course, design may be made such that the measurement is not automatic but a measurement switch is discretely provided and is operated after alignment has been completed. If design is made such that the measurement switch, if operated, does not function or is rendered inoperable until alignment is completed, it will never happen that measurement is started by a wrong operation.

Also, here, A, A0 and A1 is indicated by straight lines and C1 is indicated by a circle, whereas these shapes are not restrictive, but for example, a rectangular area may be set and control can be effected so that R1 and R2 may enter this rectangular area, to thereby accomplish similar control.

Figure 6:
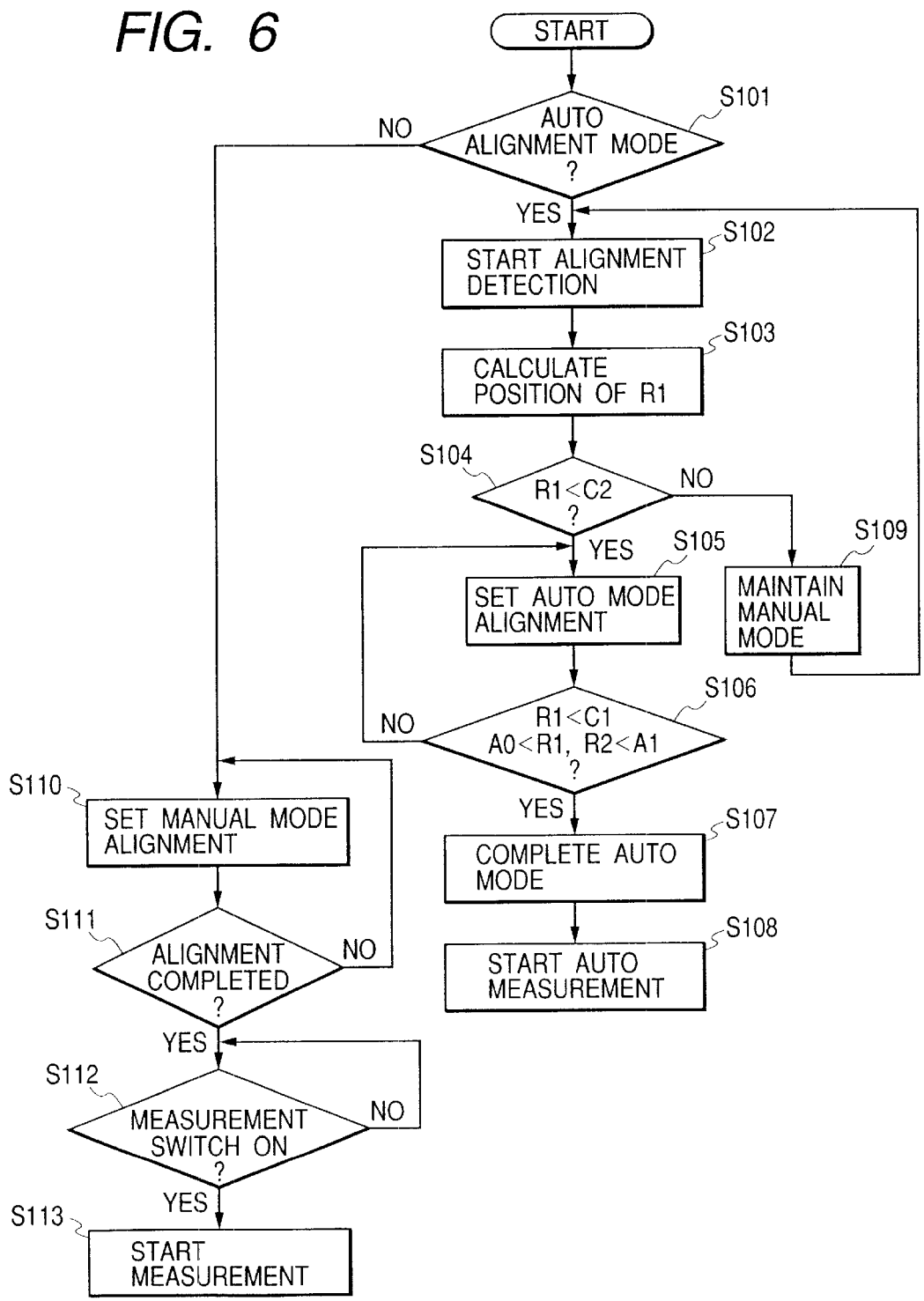
FIG. 6 is a flow chart of a third embodiment of the present invention.

The algorism described above will now be further described with reference to the flow chart of FIG. 6.

When the measuring system is moved, at S101, whether the mode changeover device 7 is set to the auto alignment mode is judged.

If it is not in the auto alignment mode, it is set to the manual alignment mode in S110. In the manual alignment, the examiner operates the operation device 5 to thereby effect alignment adjustment, and when he confirms by the visual confirmation of the monitor that the alignment has been completed, at S112, he operates the measurement switch 4, whereby the measurement of the eye to be examined is effected. Of course, in the manual alignment mode as well, the alignment detecting means may be operated, and when alignment is manually completed, display may be effected on the monitor. The start of measurement may also be automatically effected when the calculating means 30 judges the completion of the alignment.

When at S101, it is detected that the mode changeover device is set to the auto alignment mode, the alignment light source 17 is turned on and at S102, the detection of the alignment is started. At S103, the coordinates of R1 on the monitor screen is calculated. At S104, whether the coordinates of R1 are within the possible range C2 of auto alignment is calculated.

When R1 is still outside the possible range C2 of auto alignment, at S109, the manual mode is maintained, and the examiner operates the operation device 5 and continues the manual alignment.

If at S104, it is judged that R1 is within the possible range C2 of auto alignment, shift is made to the auto mode of S105, and the driving mechanism 2 is controlled to thereby effect auto alignment. Also, after shift has been made to the auto mode, if it is inhibited to perform the operation of alignment by the operation device 5, the error of bringing alignment adjustment out of order by mistake can be prevented.

At S106, whether R1 is in the substantially central possible area C1 of alignment on the monitor screen and R1 and R2 are between A0 and A1 is judged.

If the above-mentioned two conditions are not satisfied, the alignment is unfinished and therefore, return is made to S105, where the auto alignment operation is continued.

If at S106, the aforementioned conditions are satisfied, the alignment is completed and at S107, the auto mode is terminated, whereafter at S108, the automatic measurement of the eye to be examined is started.

Of course, design may be made such that measurement is not effected until the measurement switch 4 is operated.

Figure 7:
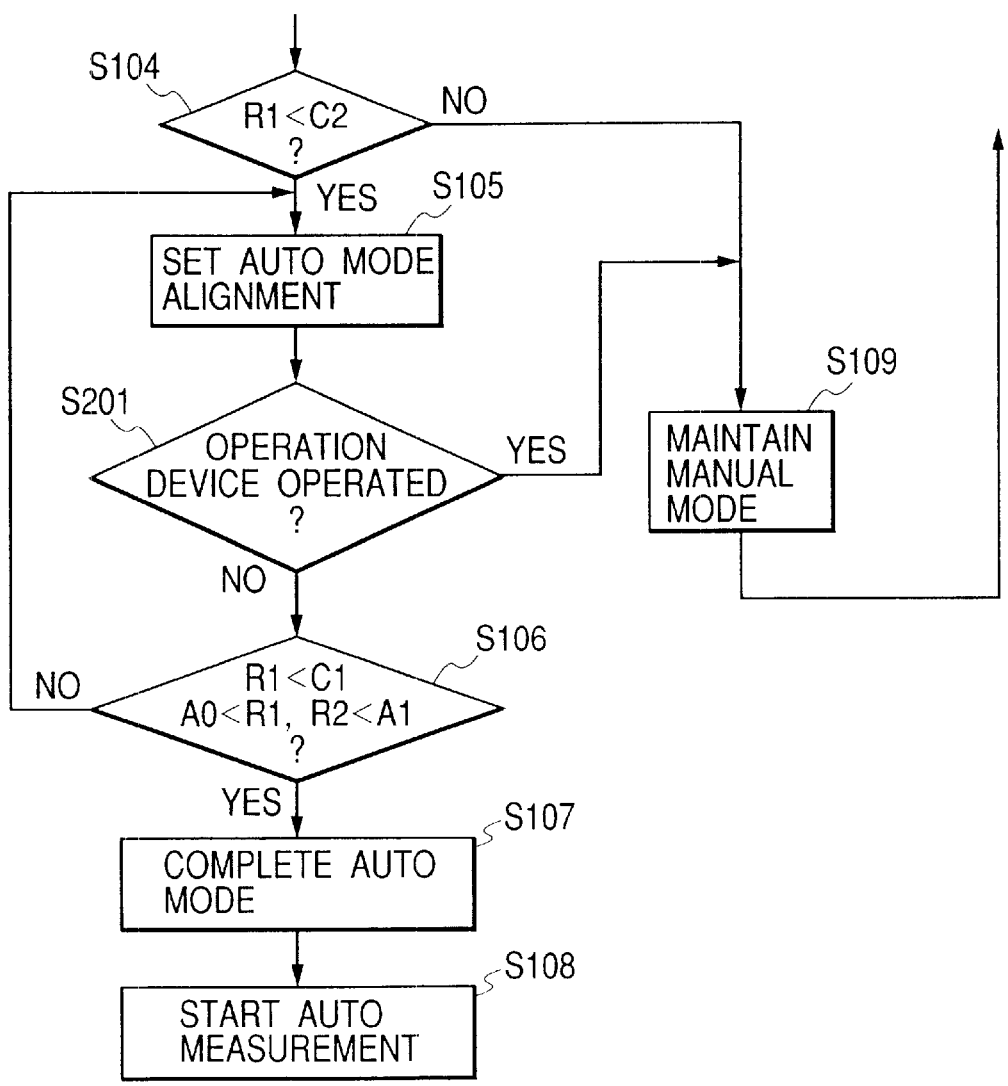
FIG. 7 is a flow chart of a fourth embodiment of the present invention.

FIG. 7 is a flow chart showing a fourth embodiment. The same portions as those in FIG. 6 need not be shown or described.

When at S201, the operation device 5 (such as a track ball) is operated during the auto mode, the mode is changed over to the manual mode (S109) and the manual operation is performed, whereafter return is made to S102, where whether R1 is in the possible area C2 of auto alignment is again judged.

Figure 8:
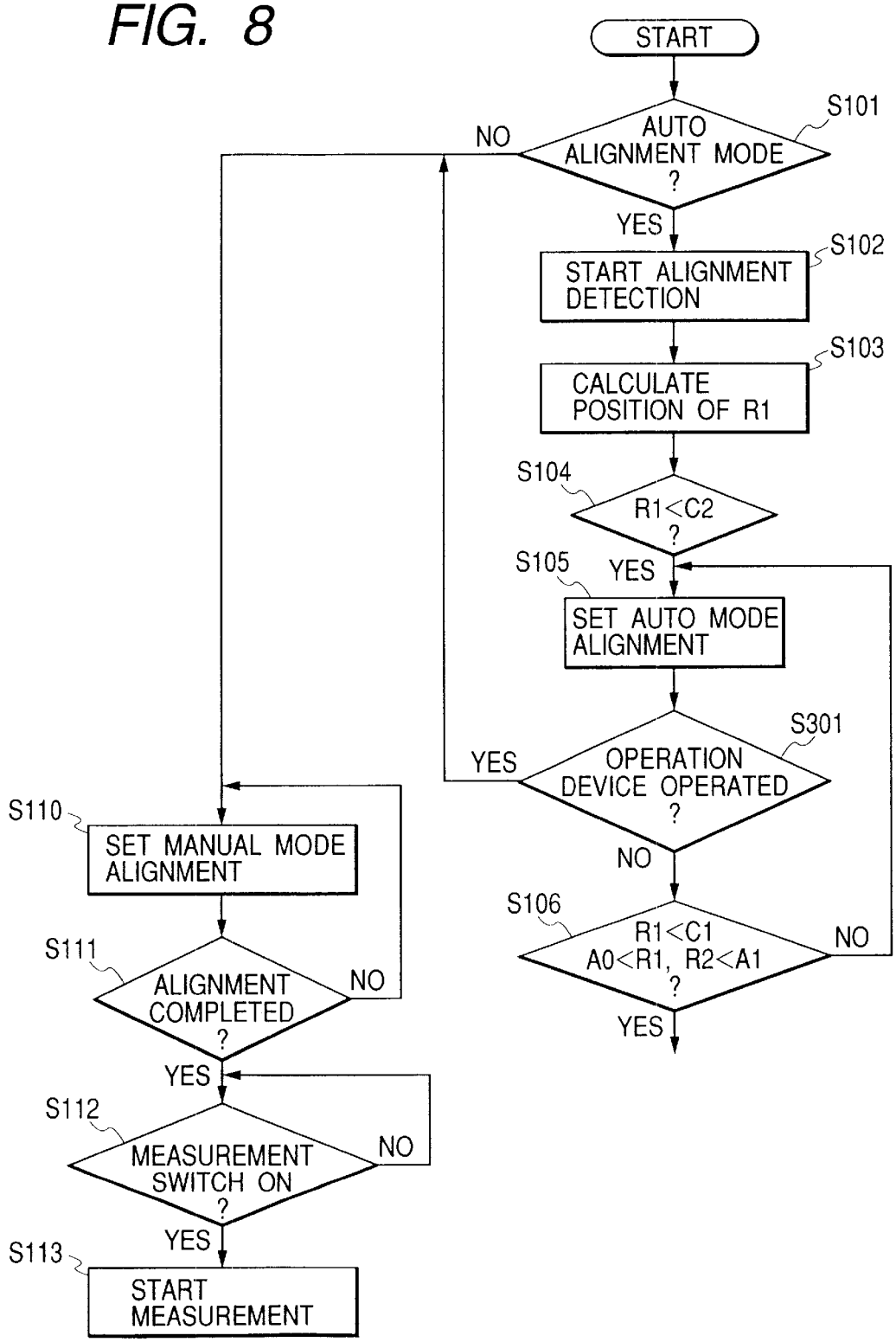
FIG. 8 is a flow chart of a fifth embodiment of the present invention.

FIG. 8 is a flow chart showing a fifth embodiment. The same portions as those in FIGS. 6 and 7 need not be shown or described.

When at S301, the operation device (such as a track ball) is operated, unlike FIG. 7, the auto alignment mode is passed through and shift is made to the manual alignment of S110. Thereafter, as described in connection with FIG. 6, the measurement of the eye to be examined is started after the manual alignment is completed.

Figure 9:
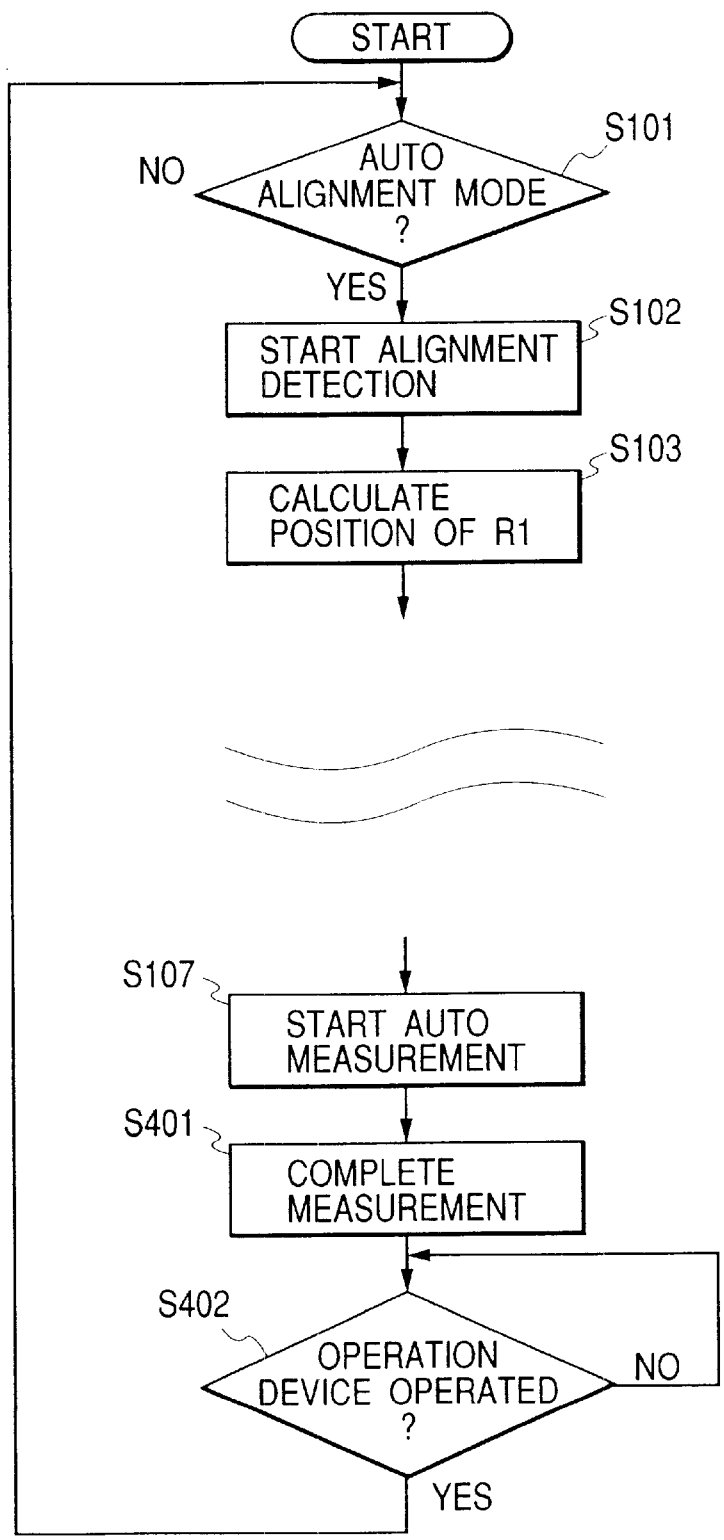
FIG. 9 is a flow chart of a sixth embodiment of the present invention.

FIG. 9 is a flow chart showing a sixth embodiment.

At S107 in the aforedescribed flow chart, the auto measurement of the eye to be examined is started, and then at S401, the measurement is completed. After the measurement has been completed, at S402, the operation device is operated, whereupon the measuring system is started again, and as in the previous measurement, return is made to S101, where the judgment of the auto alignment mode is started.

Also, while in the present flow chart, the restarting of the measuring system is effected by the operation of the operation device, the operation device is not restrictive, but a discrete switch may be provided, or design may be made such that the measuring system is restarted by the operation of the measurement switch 4.

As described above, according to the present invention, the mode can be automatically changed over from the manual mode to the auto mode and alignment can be effected smoothly. Also, when the operation device is operated by mistake during auto alignment, alignment can be prevented from being brought out of order.

Conversely, design can be made such that when the operation device is operated, the mode is changed over to the manual mode and manual adjustment is effected, whereafter in case of entering within the possible area of auto alignment, alignment can be effected in the auto mode.

Also, when the operation device is operated, it is possible to give priority to manual alignment to the last by forcibly fixing the mode to the manual alignment mode.

Also, after measurement has been completed, the next measurement can be started by operating the operation device or other switch.

Thus, it is made possible to provide an eye examining apparatus which can effect alignment and measurement very easily.

What is claimed is:

1. An ophthalmologic apparatus, comprising:
   a measuring optical system which optically measures an eye to be examined;
   a detection system which detects alignment information of the eye for the measurement;
   a driving mechanism which moves said measuring optical system relative to the eye;
   an operating device which allows an operator to manually control the driving mechanism in order to move said measuring optical system; and
   a controller which controls the driving mechanism to perform alignment of said measuring optical system with respect to the eye, with a plurality of modes including a first mode executing automatic alignment within a predetermined range based on the alignment information of said detection system and a second mode executing manual alignment within a range broader than said predetermined range based on the operation of said operating device, wherein said controller automatically its operation changes between the first mode and the second mode based on a predetermined event.

2. An apparatus according to claim 1, wherein the controller controls said apparatus, during the second mode, to change automatically from the second mode to the first mode when the detection system detects positional information which lies within said predetermined range.

3. An apparatus according to claim 1, wherein the controller controls said apparatus, during the first mode, to change automatically from the first mode to the second mode when the operating device is operated.

4. An apparatus according to claim 1, further comprising an indicator which provides a distinguishable indication of the first mode and the second mode for the operator.

5. An apparatus according to claim 1, further comprising an optical element with at least one prism disposed in an optical path of the detection system at least during the alignment and an area sensor, wherein the prism serves to separate a partial light beam and the area sensor serves to detect the position of the separated partial light beam in order to detect alignment information.

6. An apparatus according to claim 5, wherein said optical element has a plurality of said prisms, and further comprises an actuator for putting said optical element into the optical path during the alignment with said detection system and for putting said optical element out of the optical path during the measurement with said measuring optical system.

7. An apparatus according to claim 6, further comprising an aperture selectively disposed, during the measurement, within the optical path of the measurement optical system independently of said optical element.

8. An apparatus according to claim 5, wherein said optical element has an aperture for the measurement with said measuring optical system, and a plurality of said prisms disposed around the aperture for the alignment with said detection system.

9. An apparatus according to claim 1, wherein said controller serves to automatically start the measurement with said measurement optical system after the alignment with said detection system.

10. An apparatus according to claim 9, wherein the controller controls the mode so as to change from the first mode to the second mode when said operating device is operated after measurement has been completed.

11. An apparatus according to claim 1, wherein said measuring optical system includes a system to measure at least one of a refractive power and the cornea of said eye to be examined.

12. An apparatus according to claim 1, said measuring optical system and said detection system have a lens and an area sensor, being used both for a cornea measurement by said measuring optical system and for a three-dimensional alignment detection by said detection system.

13. An apparatus according to claim 1, wherein the controller controls, during the second mode, to inhibit the mode from changing over from the second mode to the first mode when the operating device is operated.

14. An apparatus according to claim 1, wherein the controller renders the start of measurement inhibited until alignment is completed.

15. An ophthalmologic apparatus, comprising:
    a measuring optical system which optically measures a cornea of an eye to be examined; and
    a detection system which detects three-dimensional alignment information of the eye,
    wherein the measuring optical system and the detection system have a lens and an area sensor, being used both for a cornea measurement by said measuring optical system and for a three-dimensional alignment detection by said detection system.

16. A method for measuring an eye to be examined, using an ophthalmologic apparatus and comprising the steps of:
    the first step of manually effecting the alignment of a measuring optical system and an eye to be examined;
    the second step of automatically effecting alignment after alignment has been completed up to a predetermined area; and
    the third step of effecting measurement after auto alignment has been completed.

17. A method apparatus according to claim 16, further comprising:
    the fourth step of again measuring optical system and the eye to be examined possible after the measurement has been completed.

* * * * *